United States Patent
Lowery, Jr. et al.

(10) Patent No.: US 8,421,458 B2
(45) Date of Patent: Apr. 16, 2013

(54) NMR DIAGNOSTICS BY MEANS OF A PLASTIC SAMPLE CONTAINER

(75) Inventors: Thomas J. Lowery, Jr., Belmont, MA (US); Robert Palazzolo, Boxborough, MA (US)

(73) Assignee: T2 Biosystems, Inc., Cambridge, MA (US)

(*) Notice: Subject to any disclaimer, the term of this patent is extended or adjusted under 35 U.S.C. 154(b) by 420 days.

(21) Appl. No.: 12/680,670

(22) PCT Filed: Sep. 29, 2008

(86) PCT No.: PCT/US2008/011240
§ 371 (c)(1),
(2), (4) Date: Aug. 10, 2010

(87) PCT Pub. No.: WO2009/045354
PCT Pub. Date: Apr. 9, 2009

(65) Prior Publication Data
US 2010/0301858 A1  Dec. 2, 2010

Related U.S. Application Data

(60) Provisional application No. 60/995,724, filed on Sep. 28, 2007.

(51) Int. Cl.
*G01R 33/44* (2006.01)
(52) U.S. Cl.
USPC ................ 324/309; 324/307; 435/6.1
(58) Field of Classification Search ............ 324/309
See application file for complete search history.

(56) References Cited

U.S. PATENT DOCUMENTS

| | | | |
|---|---|---|---|
| 3,987,361 | A | 10/1976 | Martin, Jr. et al. |
| 4,101,435 | A | 7/1978 | Hasegawa et al. |
| 4,424,487 | A | 1/1984 | Lauffer |
| 4,452,773 | A | 6/1984 | Molday |
| 4,875,486 | A | 10/1989 | Rapoport et al. |
| 4,920,061 | A | 4/1990 | Poynton et al. |
| 5,049,819 | A | 9/1991 | Dechene et al. |
| 5,136,095 | A | 8/1992 | Tarnowski et al. |
| 5,164,297 | A | 11/1992 | Josephson et al. |
| 5,204,457 | A | 4/1993 | Maruno et al. |
| 5,254,460 | A | 10/1993 | Josephson et al. |
| 5,262,176 | A | 11/1993 | Palmacci et al. |

(Continued)

FOREIGN PATENT DOCUMENTS

| WO | WO-90/06045 A2 | 6/1990 |
|---|---|---|
| WO | WO-91/17428 A1 | 11/1991 |

(Continued)

OTHER PUBLICATIONS

Atanasijevic et al., "Calcium-sensitive MRI contrast agents based on superparamagnetic iron oxide nanoparticles and calmodulin," *Proc Natl Acad Sci USA*. 103(40): 14707-12, 2006.

(Continued)

*Primary Examiner* — Melissa Koval
*Assistant Examiner* — Rishi Patel
(74) *Attorney, Agent, or Firm* — Clark & Elbing LLP

(57) ABSTRACT

Sample containers and methods for employing the same in in-vitro nuclear magnetic resonance measurements are provided. The sample containers are made of a material that comprises one or more polymeric materials.

5 Claims, 13 Drawing Sheets

U.S. PATENT DOCUMENTS

| | | | |
|---|---|---|---|
| 5,424,419 | A | 6/1995 | Hasegawa et al. |
| 5,445,970 | A | 8/1995 | Rohr |
| 5,445,971 | A | 8/1995 | Rohr |
| 5,492,814 | A | 2/1996 | Weissleder |
| 5,801,003 | A | 9/1998 | Shimamura et al. |
| 6,013,188 | A | 1/2000 | Terstappen et al. |
| 6,054,857 | A | 4/2000 | Doty |
| 6,165,378 | A | 12/2000 | Maruno et al. |
| 6,194,900 | B1 | 2/2001 | Freeman et al. |
| 6,294,342 | B1 | 9/2001 | Rohr et al. |
| 6,297,062 | B1 | 10/2001 | Gombinski |
| 6,333,629 | B1 * | 12/2001 | Pykett et al. ............. 324/307 |
| 6,342,396 | B1 | 1/2002 | Perrin et al. |
| 6,361,944 | B1 | 3/2002 | Mirkin et al. |
| 6,500,343 | B2 | 12/2002 | Siddiqi |
| 6,599,498 | B1 | 7/2003 | Groman et al. |
| 6,630,355 | B1 | 10/2003 | Pivarnik et al. |
| 6,759,601 | B1 * | 7/2004 | Petty et al. ............. 177/1 |
| 6,767,635 | B1 | 7/2004 | Bahr et al. |
| 6,768,305 | B1 | 7/2004 | Keifer |
| 6,866,838 | B1 | 3/2005 | Mondain-Monval et al. |
| 6,940,378 | B2 | 9/2005 | Miller et al. |
| 7,001,589 | B2 | 2/2006 | Mondain-Monval et al. |
| 7,018,849 | B2 | 3/2006 | Piasio et al. |
| 7,217,457 | B2 | 5/2007 | Elaissari et al. |
| 7,217,542 | B2 | 5/2007 | Tyvoll et al. |
| 7,553,542 | B2 | 6/2009 | Ou et al. |
| 7,564,245 | B2 | 7/2009 | Lee |
| 7,781,228 | B2 | 8/2010 | Menon et al. |
| 7,829,350 | B2 | 11/2010 | Josephson et al. |
| 2003/0092029 | A1 * | 5/2003 | Josephson et al. ............. 435/6 |
| 2003/0222648 | A1 | 12/2003 | Fan |
| 2005/0024055 | A1 | 2/2005 | Cavaluzzi et al. |
| 2005/0280415 | A1 | 12/2005 | Hofmann et al. |
| 2007/0166730 | A1 * | 7/2007 | Menon et al. ............. 435/6 |
| 2008/0204022 | A1 | 8/2008 | Sillerud et al. |
| 2008/0305048 | A1 | 12/2008 | Josephson et al. |
| 2009/0099342 | A1 | 4/2009 | Braconnot et al. |
| 2010/0072994 | A1 | 3/2010 | Lee et al. |
| 2010/0120174 | A1 | 5/2010 | Josephson et al. |

FOREIGN PATENT DOCUMENTS

| | | |
|---|---|---|
| WO | WO-98/04740 A1 | 2/1998 |
| WO | WO-99/67606 A1 | 12/1999 |
| WO | WO-01/00876 A1 | 1/2001 |
| WO | WO-01/19405 A2 | 3/2001 |
| WO | WO-02/98364 A2 | 12/2002 |
| WO | WO-2004/104601 A2 | 12/2004 |
| WO | WO-2005/61724 A1 | 7/2005 |
| WO | WO-2005/99419 A2 | 10/2005 |
| WO | WO-2007/27843 A2 | 3/2007 |
| WO | WO-2008/119054 A1 | 10/2008 |
| WO | WO-2008/137721 A2 | 11/2008 |
| WO | WO-2009/17697 A2 | 2/2009 |
| WO | WO-2009/26251 A1 | 2/2009 |
| WO | WO-2009/61481 A1 | 5/2009 |
| WO | WO-2009/85214 A1 | 7/2009 |
| WO | WO-2010/02479 A1 | 1/2010 |
| WO | WO-2010/51362 A1 | 5/2010 |

OTHER PUBLICATIONS

Demas et al., "Portable, low-cost NMR with laser-lathe lithography produced microcoils," *J Magn Reson.* 189(1):121-9, 2007.

Communication enclosing Office Action for European Application No. 08 836 011.0 dated Jun. 12, 2012 (12 pages).

Costanzo et al., "Protein-ligand mediated aggregation of nanoparticles: a study of synthesis and assembly mechanism," 16(9):1775-85, 2004.

Fry et al., "A new approach to template purification for sequencing applications using paramagnetic particles," *Biotechniques.* 13(1):124-31, 1992.

Gijs, "Magnetic bead handling on chip: new opportunities for analytical applications," *Microfluid Nanofluid* 1:22-40, 2004.

International Preliminary Report on Patentability for International Application No. PCT/US2008/011240, dated Mar. 30, 2010 (11 pages).

Josephson et al., "High-efficiency intracellular magnetic labeling with novel superparamagnetic-Tat peptide conjugates," *Bioconjug Chem.* 10(2):186-91, 1999.

Kim et al., "Magnetic relaxation switch detection of human chorionic gonadotrophin," *Bioconjug Chem.* 18(6):2024-8, 2007.

Kötitz et al., "Determination of the biding reaction between avidin and biotin by relaxation measurements of magnetic nanoparticles," *Journal of Magnetism and Magnetic Materials* 194:62-8, 1999.

Kriz et al., "Advancements toward magneto immunoassays," *Biosens Bioelctron.* 13(7-8)817-23, 1998.

Kriz et al., "Magnetic permeability measurements in bioanalysis and biosensors," *Anal Chem.* 68(11):1966-70, 1996.

Lee et al., "Microelectromagnets for the control of magnetic nanoparticles," *Appl Phys Letters* 79(20):3308-10, 2001.

Lewin et al., "Tat peptide-derivatized magnetic nanoparticles allow in vivo tracking and recovery of progenitor cells," *Nat Biotechnol.* 18(4): 410-4, 2000.

International Search Report for International Application No. PCT/US2008/011240, dated Feb. 2, 2009 (5 pages).

Makiranta et al., "Modeling and simulation of magnetic nanoparticle sensor," Proceedings of the 2005 IEEE, Shanghai, China, Sep. 1-4, 2005, pp. 1256-1259.

Malba et al., "Laser-lathe Lithography—a novel method for manufacturing nuclear magnetic resonance microcoils," *Biomedical Microdevices* 5(1):21-7, 2003.

Massin et al., "Planar micro-coil based magnetic resonance imaging of cells," Transducers, Solid-state Sensors, Actuators and Microsystems 12th Int'l conference 2(9):967-70, 2003.

Massin et al., "Planar microcoil-based microfluidic NMR probes," *J Magn Reson.* 164(2):242-55, 2003.

Niemeyer et al., "Self-assembly of DNA-streptavidin nanostructures and their use as reagents in immuno-PCR," *Nucleic Acids Res.* 27(23):4553-61, 1999.

Perez et al., "DNA-based magnetic nanoparticle assembly acts as a magnetic relaxation nanoswitch allowing screening of DNA-cleaving agents," *J Am Chem Soc.* 124(12):2856-7, 2002.

Perez et al., "Magnetic relaxation switches capable of sensing molecular interactions," *Nat Biotechnol.* 20(8): 816-20, 2002.

Perez et al., "Use of magnetic nanoparticles as nanosensors to probe for molecular interactions," *Chembiochem.* 5(3):261-4, 2004.

Perez et al., "Viral-induced self-assembly of magnetic nanoparticles allows the detection of viral particles in biological media," *J Am Chem Soc.* 125(34):10192-3, 2003.

Seiter et al., "Delayed fourier transform proton magnetic resonance spectroscopy," *J Am Chem Soc.* 94(7): 2535-37, 1972.

Shapiro et al., "Dynamic imaging with MRI contrast agents: quantitative considerations," *Magn Reson Imaging.* 24(4): 449-62, 2006.

Sillerud et al., "1H NMR Detection of superparamagnetic nanoparticles at 1T using a microcoil and novel tuning circuit," *J Magn Reson.* 181(2):181-90, 2006.

Sun et al., "Continuous analyte sensing with magnetic nanoswitches," *Small.* 2(10):1144-7, 2006.

Syms et al., "MEMS Helmholtz coils for magnetic resonance imaging," *J. Micromech. Microeng.* 15:S1-S9, 2005.

Tong et al., "Coating optimization of superparamagnetic iron oxide nanoparticles for high T2 relaxivity," *Nano Lett.* 10(11):4607-13, 2010.

Tsourkas et al., "Magnetic relaxation switch immunosensors detect enantiomeric impurities," *Angew Chem Int Ed Engl.* 43(18): 2395-9, 2004.

Wallen et al., "A polymer NMR cell for the study of high-pressure and supercritical fluid solutions," *Anal Chem.* 72(17):4230-4, 2000.

Weissleder et al., "Cell-specific targeting of nanoparticles by multivalent attachment of small molecules," *Nat Biotechnol.* 23(11):1418-23, 2005.

* cited by examiner

NMR DIAGNOSTICS BY MEANS OF A PLASTIC SAMPLE CONTAINER

Cross Reference to Related Applications

This application is the U.S. National Stage of International Application No. PCT/US2008/011240, filed Sep. 29, 2008 which claims the benefit of U.S. Provisional Application No. 60/995,724, filed Sept. 28, 2007, all hereby incorporated by reference.

RELATED APPLICATION

This application claims the benefit of U.S. Provisional Application No. 60/995,724, filed on Sep. 28, 2007, the entire teachings of which are incorporated herein by reference.

BACKGROUND OF THE INVENTION

Nuclear magnetic resonance (NMR) measurements commonly use high-quality glass as a means of presenting the sample to the NMR device. The objective for using high-quality glass as sample container material is to prevent spurious signals due to the sample container itself and to prevent alteration of the magnetic field that would lead to changes of the NMR signals within the sample. Often the magnetic susceptibility of the sample container is matched to the magnetic susceptibility of the liquid being measured to ensure minimal interference with the magnetic field uniformity.

In-vitro medical diagnostics using NMR rely on obtaining a few NMR parameters from the sample in a reliable and robust manner and require sample containers that are commonly of a more complex shape than the sample containers used in other NMR measurements. Fabrication of such sample containers is difficult and expensive.

SUMMARY OF THE INVENTION

One embodiment of the present invention is a method for obtaining a nuclear magnetic resonance parameter of a sample, wherein the nuclear magnetic resonance parameter is T1 or T2. The method comprises (a) applying a radiofrequency pulse sequence in the presence of a magnetic field to the sample and a sample container containing the sample, resulting in an NMR signal associated with the sample and an NMR signal associated with the sample container, wherein the sample container comprises a polymeric material; (b) acquiring part or all of the resulting NMR signals to obtain raw data; and (c) processing the resulting NMR signals to obtain the nuclear magnetic resonance parameter of the sample, wherein contribution of the NMR signal associated with the sample container to the nuclear magnetic resonance parameter of the sample is reduced, partly or completely.

A further embodiment of the present invention is an NMR sample container comprising a polymeric material, wherein the sample container contains a biofluid and the sample container is adapted for measuring T1 and/or T2 in a nuclear magnetic resonance device, wherein the nuclear magnetic resonance device comprises one or more radiofrequency coils with an associated detection volume.

Yet a further embodiment of the present invention is a sample container, wherein the sample container is made of a material that comprises one or more polymeric materials and the sample container is suitable for in-vitro nuclear magnetic resonance measurements.

Yet another embodiment of the present invention is a method for obtaining one or more nuclear magnetic resonance parameters of one or more samples in-vitro using a nuclear magnetic resonance device. The method comprises containing the one or more samples in a sample container within the nuclear magnetic resonance device, the sample container being made of a material that comprises one or more polymeric materials.

Yet another embodiment of the present invention is a method for obtaining T2 of one or more samples using a nuclear magnetic resonance device, wherein the nuclear magnetic resonance device comprises one or more radiofrequency coils with an associated detection volume and one or more magnets. The method comprises: positioning a sample container made of a material that comprises one or more polymeric materials within the detection volume of the one or more radiofrequency coils; applying a magnetic field provided by the one or more magnets to the sample container; applying a radiofrequency pulse sequence in the presence of the magnetic field to the sample container and one or more samples, resulting in NMR signals associated with the one or more samples and NMR signals associated with the sample container; acquiring the NMR signals to obtain raw data; and processing the raw data to obtain T2 of the one or more samples in the sample container.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

DETAILED DESCRIPTION OF THE INVENTION

Figure 1:
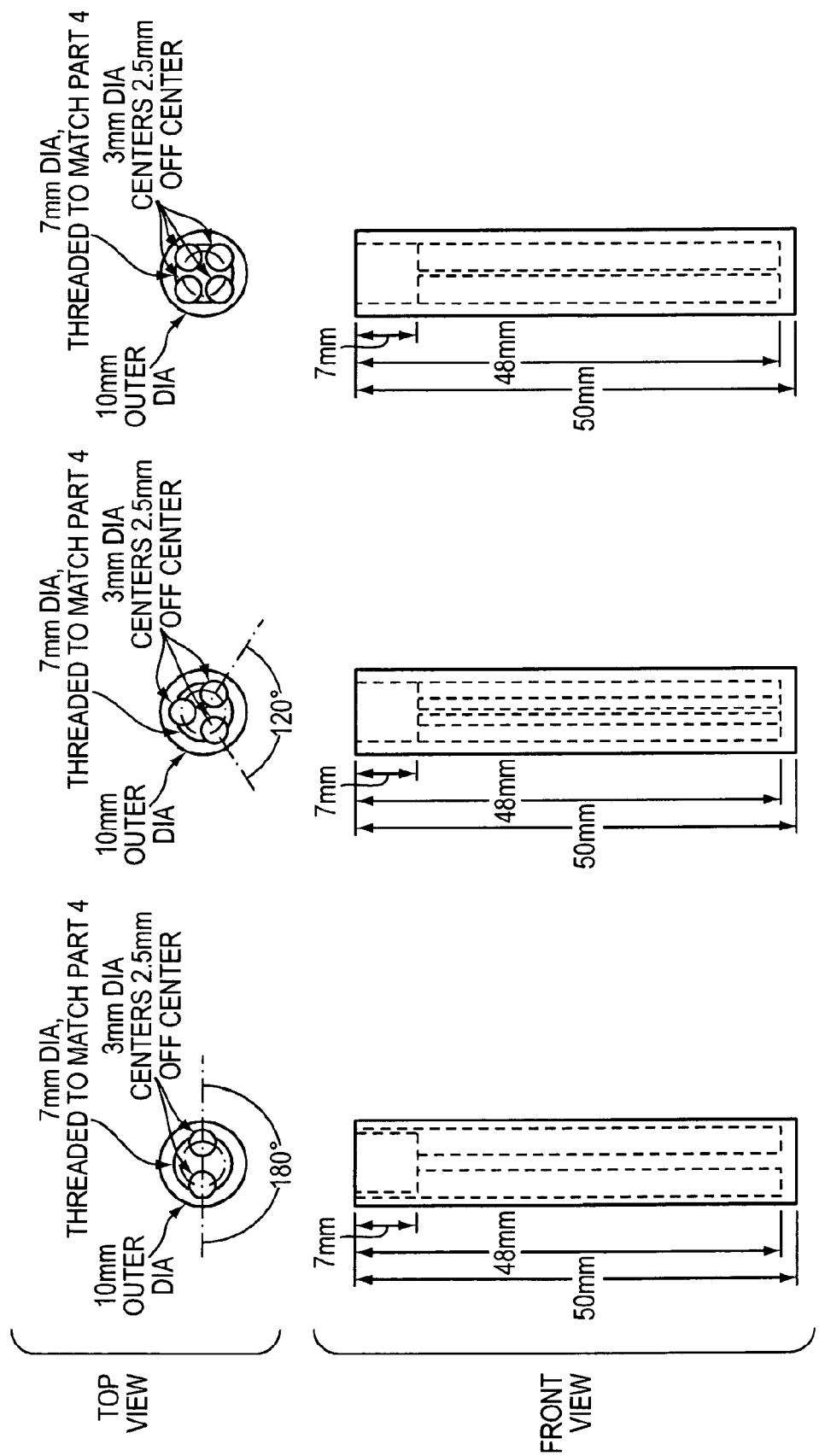
FIG. 1: Schematic representation of plastic cartridges with two (left), three (middle) and four (right) separate sample volumes of the same size.

A description of example embodiments of the invention follows.

The teachings of all patents, published applications and references cited herein are incorporated by reference in their entirety.

This invention enables the use of materials not commonly used for NMR sample containers that are much cheaper and more easily fabricated to meet requirements for the disposable microfluidic cartridges commonly used for in vitro diagnostics. It allows methods such as injection molding to be used to fabricate sample holders out of proton rich materials, such as plastics.

A "sample container" as used herein is a solid structure that is shaped such that it can contain at least one sample. Typically, the sample container is shaped and sized in view of one or more radiofrequency coils of a given device for in-vitro nuclear magnetic measurements. More typically, the sample container is shaped and sized such that the at least one sample contained therein fits at least partly into the detection volume of the one or more radiofrequency coils. Even more typically, the sample container is shaped and sized such that the at least one sample contained therein fits entirely into the detection volume of the one or more radiofrequency coils. Most typically, the sample container is shaped and sized to fit entirely into the detection volume of the one or more radiofrequency coils.

A "detection volume" as used herein, is the volume from which NMR signals from a sample can be detected in a given NMR measurement using the given radiofrequency coil, that is, any part of a given sample that is outside of the detection volume does not directly lead to detectable NMR signals.

Many different radiofrequency or NMR detection coils are known in the art. This includes "planar" coils and "whole volume" coils such as might be constructed of opposed saddle coils, solenoids, Helmholtz coils and the like. Typically, the shape of a sample container designed to fit into the detection volume of a solenoid coil is a cylinder. However, other shapes and forms are possible, for example, a sample container can be, for example, a capillary tube, a cuvette, a well, a strip, a fluidic chip, a fluidic cartridge and the like.

The sample container of the present invention can contain any number of separate volumes or sample chambers. "Separate volumes" or "sample chambers" as used herein are volumes that if filled with samples prevent mixing of the samples. Typically, the separate volumes can optionally have one or more inlets and one or more outlets. More typically, the separate volumes optionally have one inlet and one outlet. Also, optionally, the separate volumes can contain a movable barrier. A "movable barrier" as used herein, is a structure that divides a separate volume in two volumes, one volume that has at least one inlet and one volume that has at least one outlet. Typically an empty separate volume has a barrier positioned near the inlet. Upon filling of the separate volume with a sample liquid, the barrier moves through part or all of the entire separate volume thereby removing any gas through the outlet. It is believed that inclusion of a movable barrier allows better control in filling the sample container with test fluid thereby reducing partly or completely formation of gas (typically, air) bubbles during the filling process. Typically, the sample container contains between 1 and about 1000 separate volumes. More typically, the sample container contains between 1 and about 100 separate volumes. Even more typically, the sample container contains between 1 and about 10 separate volumes. Even more typically, the sample container contains between 2 and about 10 separate volumes. Even more typically, the sample container contains between 2 and 4 separate volumes. Even more typically, the sample container contains between 2 and 3 separate volumes. Most typically, the sample container contains 2 separate volumes. The "separate volumes" or "sample chambers" can have the same dimensions, different dimensions but equal volumes, or different dimensions and different volumes. Typically, each separate volume can be between about 1 fL and about 10 mL. More typically, each separate volume can be between about 1 pL and about 1 mL. Most typically, each separate volume can be between about 1 μL and about 200 μL.

The sample container of the present invention are made of a material that comprises one or more polymeric materials. Polymeric material that withstands the conditions during an NMR measurement can be used. Examples of suitable polymeric materials include but are not limited to plastics materials, for example, polyoxymethylene, polyethylene, polypropylene, ethylene/propylene copolymers, polyvinyl chloride, polyester; polyamide, polyimide, polyurethane, polyacrylonitrile, ABS, PEEK, terpolymers of acrylates, styrene and acrylonitrile, styrene/acrylonitrile, styrene/butadiene, polybutylene, polystyrene, chlorinated polyethylene, fluoropolymers such as Teflon, polycarbonate, polymethylmethacrylate, polyphenylene oxide, polypropylene oxide, phenol/formaldehyde resins, epoxy resins and the like. Typically, at least one of the polymeric materials is proton-rich. More typically, all of the one or more polymeric materials are proton-rich. Typically, "proton-rich" refers to a polymeric material that consists of more than about 10% of spin ½ nuclei (percentage by number of total nuclei of the given polymeric material). More typically, "proton-rich" refers to a polymeric material that includes more than about 20% of spin ½ nuclei, and, even more typically, of more than about 40% of spin ½ nuclei. Commonly, the spin ½ nuclei are nuclei of hydrogen but they can also be nuclei of fluorine and the like. A preferred proton-rich polymeric material is polyoxymethylene. Typically, the sample container material can be a mixture of the one or more polymeric materials and one or more other materials such as glass, or, part of the sample container material is entirely made of one or more polymeric materials and one or more other parts are made of one or more other materials such as glass. Also, typically, the material of the sample container comprises between about 5% and 100% (by weight of the sample container) of one or more polymeric materials. More typically, the material of the sample container comprises between about 10% and 100% (by weight of the sample container) of one or more polymeric materials. Even more typically, the material of the sample container comprises between about 25% and 100% (by weight of the sample container) of one or more polymeric materials. Even more typically, the material of the sample container comprises between about 50% and 100% (by weight of the sample container) of one or more polymeric materials. Even more typically, the material of the sample container comprises between about 75% and 100% (by weight of the sample container) of one or more polymeric materials. Even more typically, the material of the sample container comprises between about 90% and 100% (by weight of the sample container) of one or more polymeric materials. Most typically, the sample container is entirely made of one or more polymeric materials.

The sample container of the present invention can be fabricated using methods known in the art. Suitable methods include form or injection molding methods, and microfabrication methods for sample containers smaller than a few millimeter, for example, two-photon three-dimensional lithography.

Magnetic particles, in particular, "Nanosensors" as used herein, are paramagnetic or superparamagnetic particles, typically of nanometer scale, that comprise a polymer matrix layer about a magnetic core and/or are derivatized/functionalized with binding moieties or affinity groups for a target compound or analyte. Suitable magnetic particles such as nanosensors are disclosed in U.S. Provisional Application No. 60/904,685 entitled "Magnetic Relaxation Switch Based Detection of Glycated Hemoglobin," filed Mar. 2, 2007, and U.S. Provisional Application No. 60/912,298 entitled "Responsive Polymer-Coated Superparamagnetic Nanosensors," filed Apr. 17, 2007, the entire teachings of which are hereby incorporated by reference. The entire teachings of the following applications are incorporated by reference in their entirety: U.S. Provisional Application No. 60/952,143, filed Jul. 26, 2007 by Thomas Jay Lowery, Jr. et al.; U.S. Utility application Ser. No. 11/513,503, filed Aug. 31, 2006 by W. David Lee; U.S. Provisional Application No. 60/857,742, filed Nov. 8, 2006 by W. David Lee et al.; U.S. Provisional Application No. 60/904,685, filed Mar. 2, 2007 by Jim Koziarz et al.; U.S. Provisional Application No. 61/063,389, filed Feb. 1, 2008 by James J. Koziarz et al.; U.S. Provisional Application No. 60/919,236, filed Mar. 21, 2007 by Doug Levinson et al.; U.S. Provisional Application No. 61/063,422, filed Feb. 1, 2008 by Douglas A. Levinson et al.; U.S. Provisional Application No. 60/915,797, filed May 3, 2007 by Tom Lowery et al.; U.S. Provisional Application No. 60/912,298, filed Apr. 17, 2007 by Tom Lowery et al.; U.S. Provisional Application No. 61/066,504, filed Feb. 21, 2008 by Thomas J. Lowery, Jr. et al.; U.S. Provisional Application No. 60/937,067, filed Jun. 25, 2007 by Thomas J. Lowery, Jr. et al.; U.S. Provisional Application No. 60/995,830, filed Sep. 28, 2007 by Thomas Jay Lowery, Jr. et al.; U.S. Provisional Application No. 60/995,724, filed Sep. 28, 2007 by Thomas Jay Lowery, Jr. et al.; U.S. Provisional Application No. 61/002,021, filed Nov. 6, 2007 by Thomas J. Lowery, Jr.; U.S. Provisional Application No. 61/000,519, filed Oct. 26, 2007 by Sonia Taktak; U.S. Provisional Application No. 61/002,022, filed Nov. 6, 2007 by Pablo J. Prado et al.; U.S. Provisional Application No. 61/008,991, filed Dec. 21, 2007 by Pablo J. Prado et al.; U.S. Provisional Application No. 61/008,646, filed Dec. 21, 2007 by Thomas J. Lowery, Jr. et al.; U.S. Provisional Application No. 61/008,669, filed Dec. 21, 2007 by Thomas J. Lowery, Jr. et al.; U.S. Provisional Application entitled "Integrated Magnetic Resonance Apparatus and Single-Step Particle-Based Diagnostics by Means of a Switchable Magnetic Field" (Attorney Docket Number: 4203.1019-000), filed Mar. 4, 2008 by Pablo J. Prado et al., U.S. patent application Ser. No. 10/165,258, filed Jun. 6, 2002, U.S. patent application Ser. No. 11/431,247, filed May 9, 2006, U.S. Provisional Patent Application No. 61/127,514, filed May 14, 2008, and U.S. Provisional Patent Application No. 61/068,211, filed Mar. 5, 2008.

The sample containers of the present invention are not limited to a specific type of nuclear magnetic resonance measurements. Typically, however, they are used in in-vitro diagnostic measurements. More typically, they are used in methods that aim to obtain nuclear magnetic parameters important to in-vitro diagnostics, for example, $T_1$ and $T_2$. Also, more typically, they are used in magnetic relaxation switch based methods such as those disclosed in U.S. Provisional Application No. 60/904,685 entitled "Magnetic Relaxation Switch Based Detection of Glycated Hemoglobin," filed Mar. 2, 2007.

The sample containers of the present invention are also not limited to a specific type of nuclear magnetic resonance device. Typically, however, the nuclear magnetic device is operated at or below about 1 Tesla (T), that is, the magnetic field created by the one or more magnets of the nuclear magnetic device is at or below about 1 T. Also, typically, the nuclear magnetic device is a relaxometer as known in the art.

Other nuclear magnetic resonance devices and/or methods for which the sample container of the present invention are suitable are disclosed in U.S. application Ser. No. 11/513,503 entitled "NMR Device for Detection of Analytes," filed Aug. 31, 2006, U.S. Provisional Application No. 60/857,742 entitled "NMR Systems for Detection of Analytes", filed Nov. 8, 2006, U.S. Provisional Application No. 60/904,685 entitled "Magnetic Relaxation Switch Based Detection of Glycated Hemoglobin," filed Mar. 2, 2007, U.S. Provisional Application No. 60/919,236 entitled "Magnetic Resonance Measurement of Heme and Derivatives," filed Mar. 21, 2007, U.S. Provisional Application No. 60/915,797 entitled "Systems for Unilateral and Low Field NMR Detection Using Superparamagnetic Nanosensors," filed May 3, 2007, U.S. Provisional Application No. 60/912,298 entitled "Responsive Polymer-Coated Superparamagnetic Nanosensors," filed Apr. 17, 2007, U.S. Provisional Application No. 60/937,067 entitled "Bioanalytical Assays Using Magnetic Nanosensors," filed Jun. 25, 2007, and U.S. Provisional Application entitled "Single Coil Multiplexing for NMR Diagnostics" (attorney docket number 4203.1010-000), filed Sep. 21, 2007, the entire teachings of which are hereby incorporated by reference If a sample container is used that contains at least two different samples, each of the samples in a separate volume or sample chamber of the sample container, the method for obtaining one or more nuclear magnetic resonance parameters of one or more samples in-vitro using a nuclear magnetic resonance device may include methods for discriminating the NMR signals from the different samples. Suitable methods for mix-and-read determination of, for example, spin-spin relaxation constant $T_2$ are disclosed in U.S. Provisional Application entitled "Single Coil Multiplexing for NMR Diagnostics" (attorney docket number 4203.1010-000), filed Sep. 21, 2007, the entire teachings of which are hereby incorporated by reference.

A "radiofrequency pulse sequence" as used herein is a sequence of radiofrequency pulses, the pulse characteristics including frequency of the radiofrequency pulses selected such that application of the radiofrequency pulse sequence to part or all of the sample container leads to NMR signal that can be acquired and is associated with at least one sample contained in the sample container, the acquired raw data allowing processing to obtain one or more nuclear magnetic parameters associated with the sample. Data or NMR signal acquisition can start one or more times before, during and/or after the radiofrequency pulse sequence is applied. Typically, data or NMR signal acquisition starts between pulses of the radiofrequency pulse sequence. Standard radiofrequency pulse sequences that are suitable are known in the art, for example, the Carr-Purcell-Meiboom-Gill (CPMG) is traditionally used if relaxation constant $T_2$ is to be determined. Optimization of the radiofrequency pulse sequences, including selection of the frequency of the radiofrequency pulses in the sequence, depends on the system under investigation and is performed using procedures known in the art. The radiofrequency pulse sequences of the present invention may combine pulse sequences known in the art with one or more filter radiofrequency pulse sequence to allow determination of nuclear magnetic resonance parameters of a sample in the presence of one or more additional samples. Suitable filter radiofrequency pulses are disclosed in U.S. Provisional Application entitled "Single Coil Multiplexing for NMR Diagnostics" (attorney docket number 4203.1010-000), filed Sep. 21, 2007.

Examples

Figure 2:
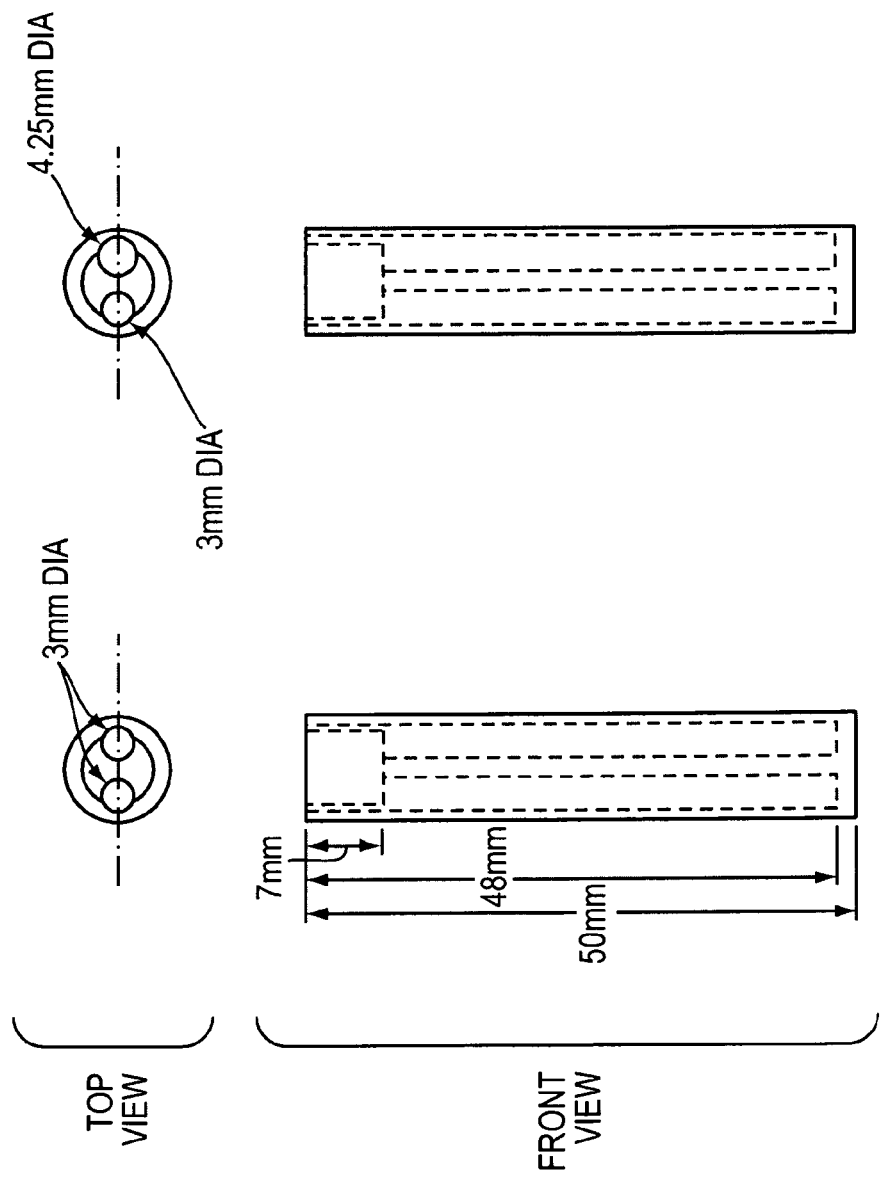
FIG. 2: Schematic representation of a plastic cartridge with two separate sample volumes of the same volume (left) and of different volumes (right).

Sample containers (also referred to as "sample cartridges") made of Delrin (polyoxymethylene; obtained from McMaster-Carr) were fabricated by machining. Several designs were fabricated for the purpose of developing single coil multiplexing. The designs are shown in FIGS. 1 and 2. These plastic cartridges were designed to fit a solenoid coil made for 10 mm glass NMR tubes, hence their cylindrical shape.

Figure 3:
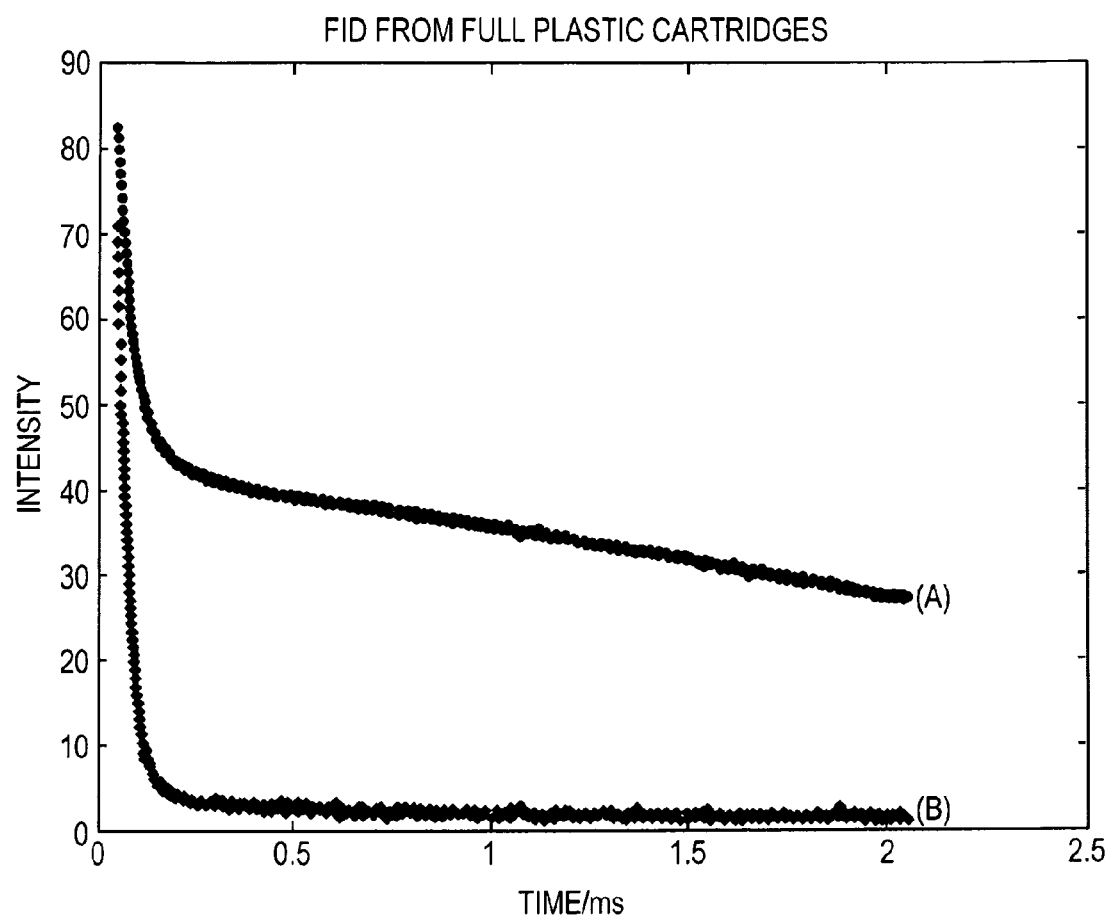
FIG. 3: Graphical representation of the time-domain signal of an empty plastic cartridge (bottom curve) and of a plastic cartridge filled with $CuSO_4$ solution (top curve).

Polyoxymethylene is a proton-rich plastic, therefore there is a resultant NMR signal when the empty cartridge is inside an NMR detection coil. The time-domain signal after a 90° pulse on an empty plastic cartridge is shown in FIG. 3 (curve B). It is believed that because the protons in the plastic are in the solid phase, they are immobile and their signal decays rapidly. As can be seen from FIG. 3 (see curve B, bottom), for this type of plastic the signal has nearly disappeared after 0.5 ms. FIG. 3 also shows signal obtained from a plastic cartridge containing 120 µL of a $CuSO_4$ solution. As can be seen, the rapidly decaying plastic signal is still present, but a slowly decaying water signal is also present (see curve A, top). The sampling time was not adequate to collect the entire water signal in this case as is apparent from the ~30% amplitude after 2 ms. To only measure the NMR signal from the liquid inside of a plastic tube the liquid signal (i.e., signal associated with the liquid) must be discriminated from the plastic signal (i.e., signal associated with the sample container). One way of achieving this is to introduce a delay after application of an acquisition radiofrequency (RF) pulse to the plastic tube and liquid therein and prior to turning on the ADC and acquiring the signal. For example, waiting 1 ms after a 90° radiofrequency pulse for the experiment in FIG. 3 would entirely remove the plastic signal. Another way to achieve this discrimination includes acquiring the NMR signals associated with both the plastic tube and the liquid and removing the plastic signal during postprocessing, that is, while processing the raw data corresponding to the combined NMR signals.

Figure 4:
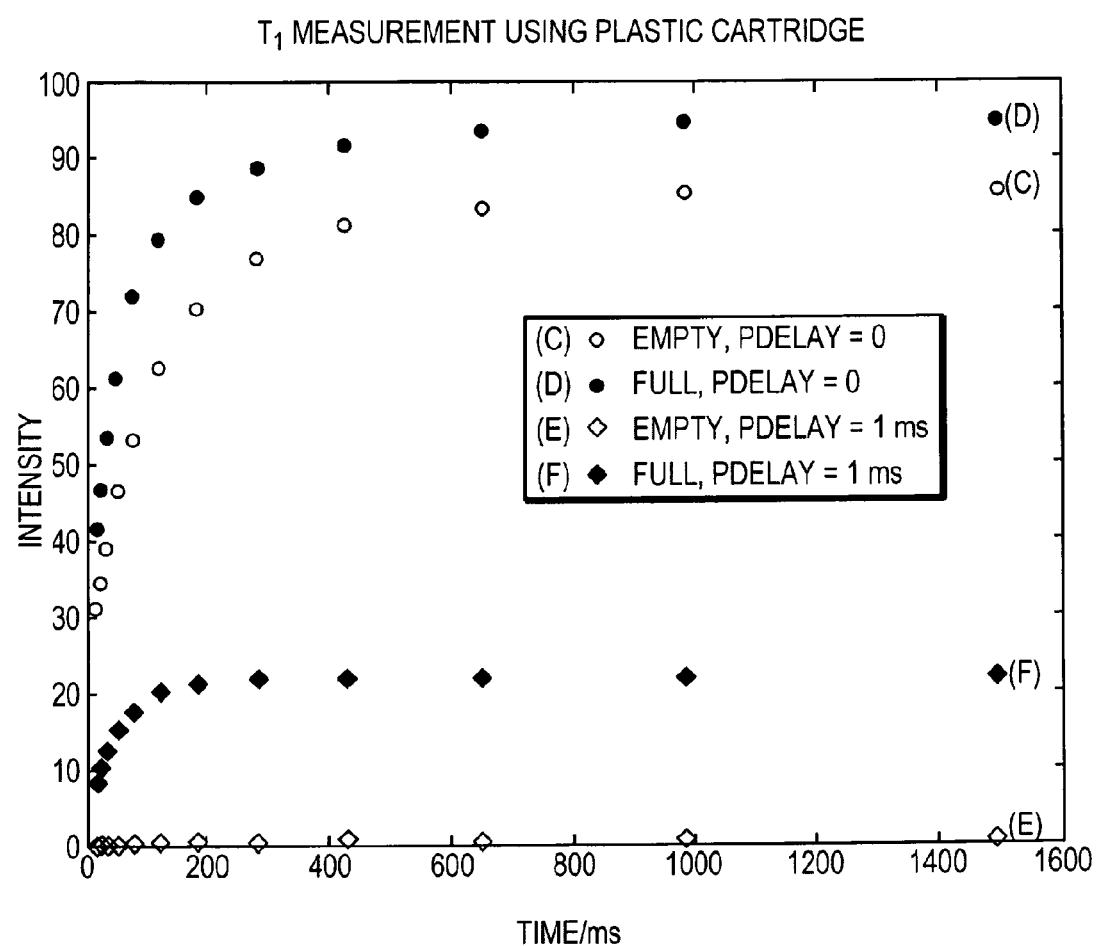
FIG. 4: Graphical representation of $T_1$ measurements on full and empty plastic cartridges.

One example of how a plastic signal can interfere with measuring signal from a liquid solution is shown in FIG. 4. In this experiment the $T_1$ relaxation constant was measured using a standard saturation recovery pulse sequence. When the total signal was acquired on an empty and a full sample cartridge without removing the signal arising from the sample cartridge material (here, polyoxymethylene; empty cartridge signified by the letter "C" and full cartridge signified by the letter "D"), the $T_1$ values of the empty and full cartridges were 128 ms and 82 ms, respectively. The large amplitude for the empty cartridge (signified by the letter "C") represented the plastic signal. The small increase in amplitude when the cartridge was filled corresponds to the water signal. When an appropriate sampling delay (that is, a delay after application of the RF pulse and prior to signal acquisition) was used to collect only the signal from the water then the $T_1$ values for the empty (signified by the letter "E") and full (signified by the letter "F") cartridges were zero and 55 ms, respectively. The amplitude of the empty cartridge was zero and that for the full cartridge was about 20%, which corresponds to only the water signal.

Figure 5:
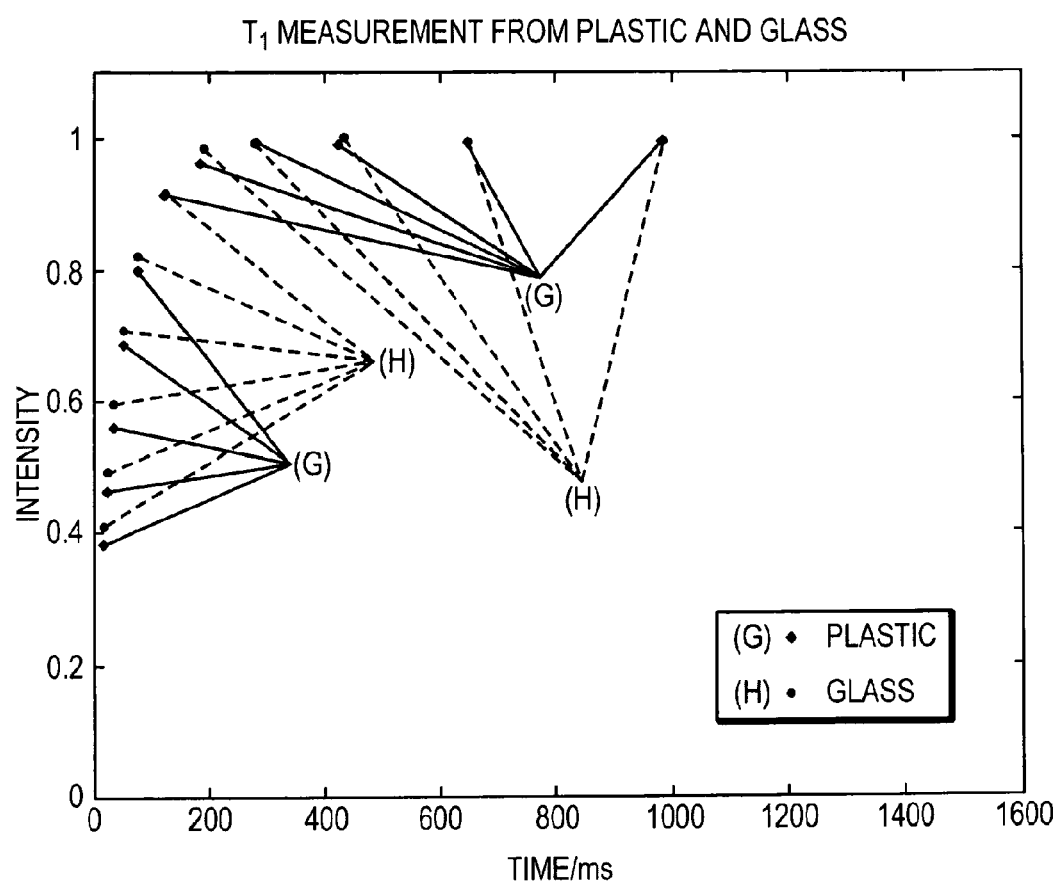
FIG. 5: Graphical representation of $T_1$ measurements for the same solution in a glass and a plastic cartridge.

In another example, the signal measured in a polyoxymethylene plastic cartridge was compared to the signal measured in a state-of-the art NMR glass tube. The data for each sample tube was normalized and plotted in FIG. 5. As can be seen, the data is practically identical. Fitting this data resulted in $T_1$ values of 53 ms for glass (signified by the letter "H") and 55 ms for plastic (signified by the letter "H").

Figure 6:
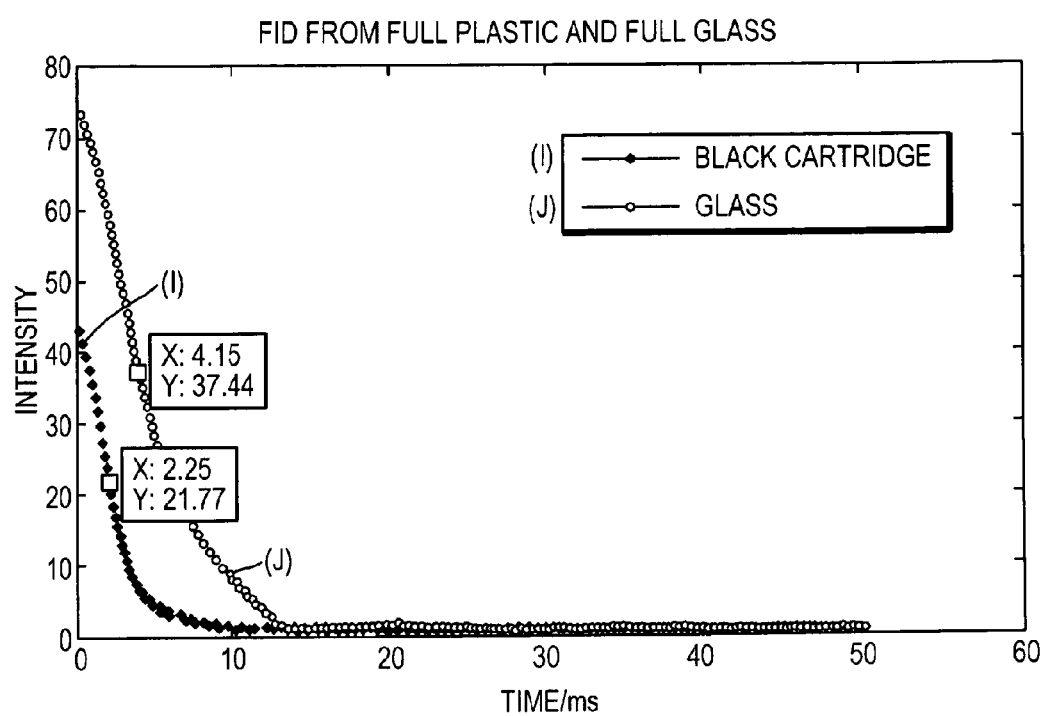
FIG. 6: Graphical representation of the free induction decay signals for the same water solution in glass tube and plastic cartridge; the half-height signal for each sample is indicated in the graph.
Figure 7:
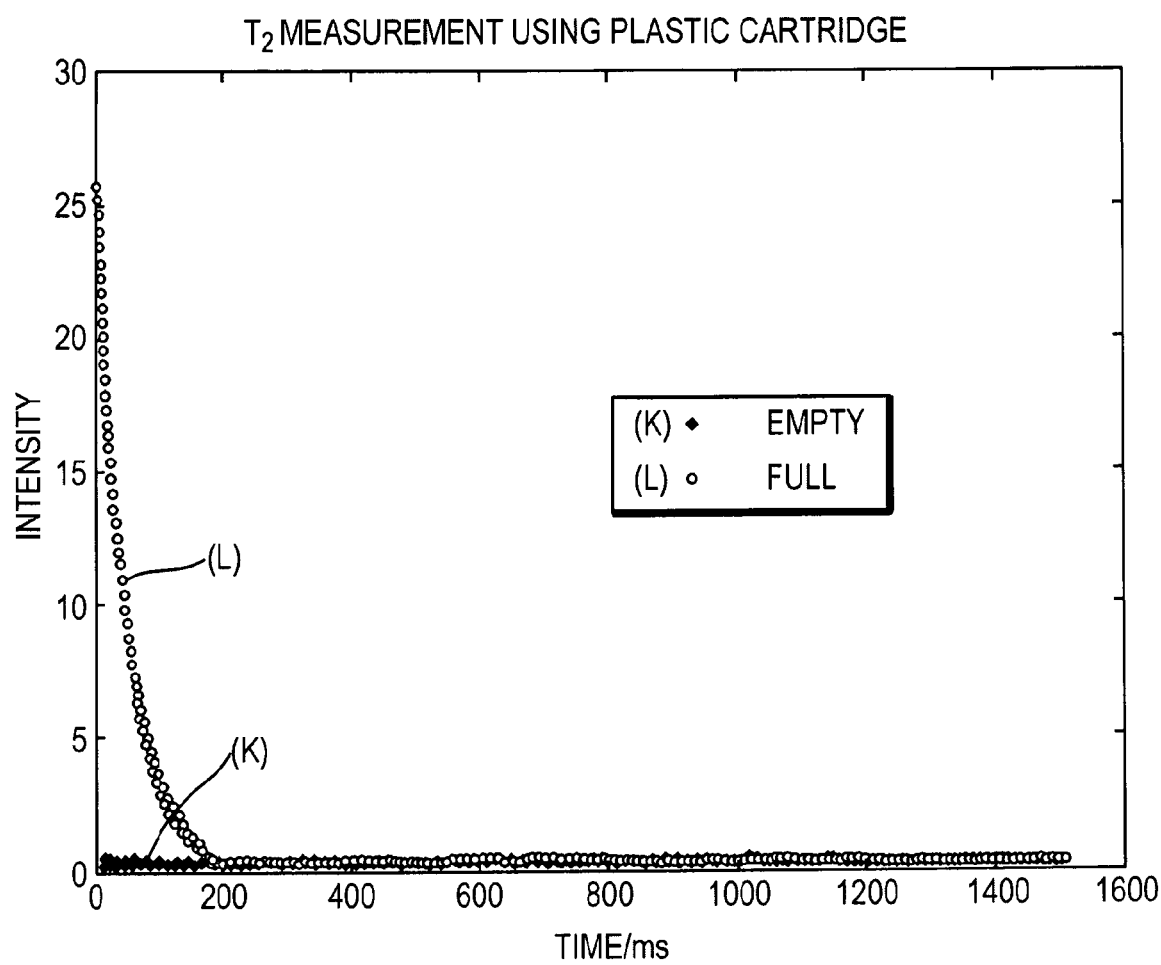
FIG. 7: Graphical representation of the $T_2$ CPMG decay curves of a plastic tube with and without sample in it.
Figure 8:
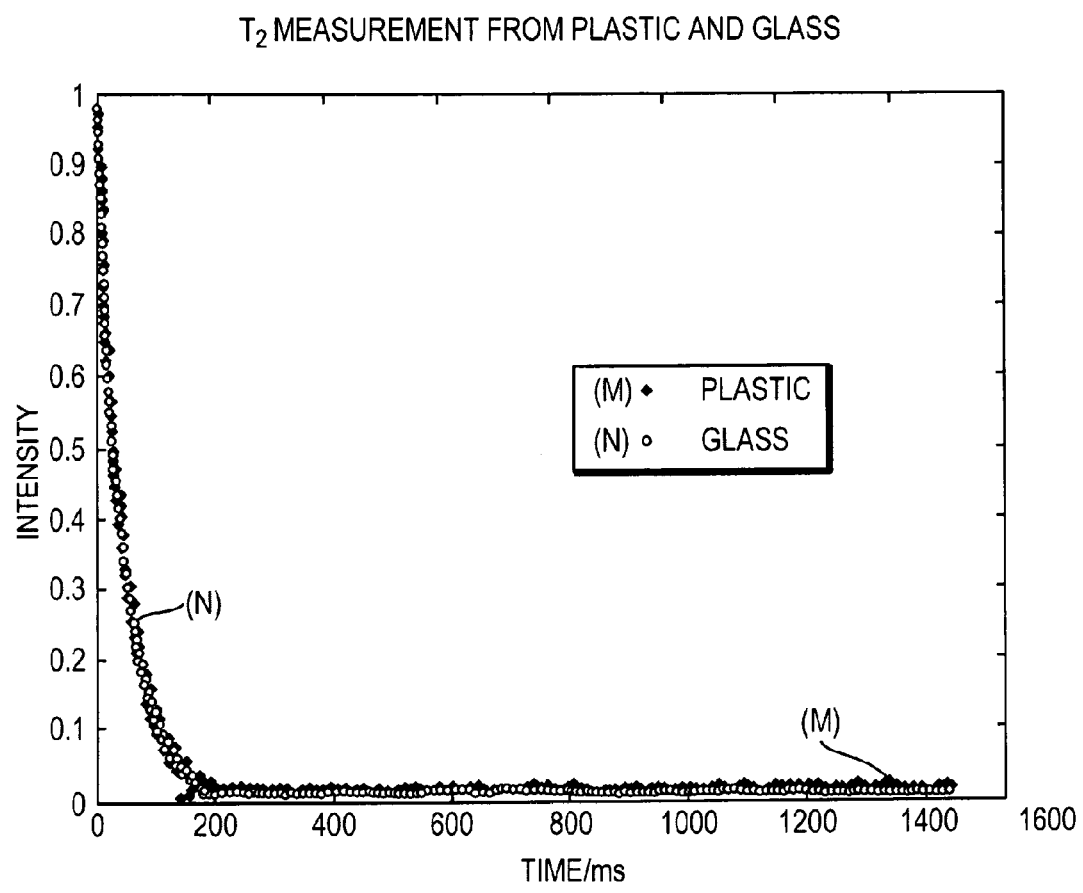
FIG. 8: Graphical representation of the $T_2$ CPMG decay curves of the same solution acquired in a glass and a plastic tube.

Inhomogeneous broadening of the NMR signals may arise if a sample tube perturbs the homogeneity of the magnetic field, thereby introducing artifacts and limiting the quality of the NMR data that can be acquired. This phenomenon is the primary motivation for high-field biomolecular spectroscopy to use very high quality glass, to prevent the sample tube from broadening the signals and diminishing resolution. One way to measure the homogeneity of the magnetic field experienced by a sample is to measure the half-height time for the free-induction decay signal. The more homogeneous the field, the longer the free-induction decay will last. FIG. 6 shows the free induction decay signals for the same solution in a polyoxymethylene tube (signified by the letter "I") and glass (signified by the letter "J"). The plastic signal decays within the first millisecond and cannot be seen on this scale. The half-height point for each decay curve is shown. The field homogeneity can be calculated from the half-height point with $$\Delta\delta(ppm) = \frac{10^6}{t_{hh}\omega_o} \quad (1)$$

where $\Delta\delta$ is the homogeneity in ppm, $t_{hh}$ is the time at which the free induction decay signal is at half-height, and $\omega_o$ is the larmour frequency ($19.95 \times 10^6$ Hz) for this system). Accordingly, the homogeneity of the magnetic field for the glass tubes is 12 ppm and that for the plastic tube is 22 ppm. Magnetic field homogeneity is very important for many applications in magnetic resonance. However, the spin-spin relaxation constant $T_2$ of a sample, which is an essential parameter for in vitro NMR diagnostics, can be determined accurately, even if the sample is contained in a plastic sample container. It is believed that this is, because during a $T_2$ measurement, magnetic field inhomogeneities are refocused such that only the microscopic inhomogeneities of the sample contribute to the $T_2$ signal. FIG. 7 shows standard Carr-Purcell-Meiboom-Gill (CPMG) $T_2$ decay curves acquired for a plastic (here, polyoxymethylene) tube with (signified by the letter "L") and without sample (signified by the letter "K"). As can be seen, only a very small signal is measured for the empty tube. In fact, fitting the data shows that the signal amplitude for the empty tube is 36 times lower than that for the full tube. It is believed that this is, because the $T_2$ relaxation rate of protons within the plastic is much faster (~2 ms) than that of protons in the liquid (50 ms). Therefore, the signal from the plastic decays to almost zero at the beginning of the CPMG decay curve. This small residual signal can be removed by not collecting the first few echoes or by excluding the data points from fitting. A comparison of the $T_2$ CPMG curve acquired with the plastic tube (signified by the letter "M") and with the glass tube (signified by the letter "N") shows that they are practically equivalent (FIG. 8). Fitting these curves yields a $T_2$ of 47 ms for plastic and 48 ms for glass showing that $T_2$ values can be accurately detected for samples contained in a polyoxymethylene tube.

Figure 9:
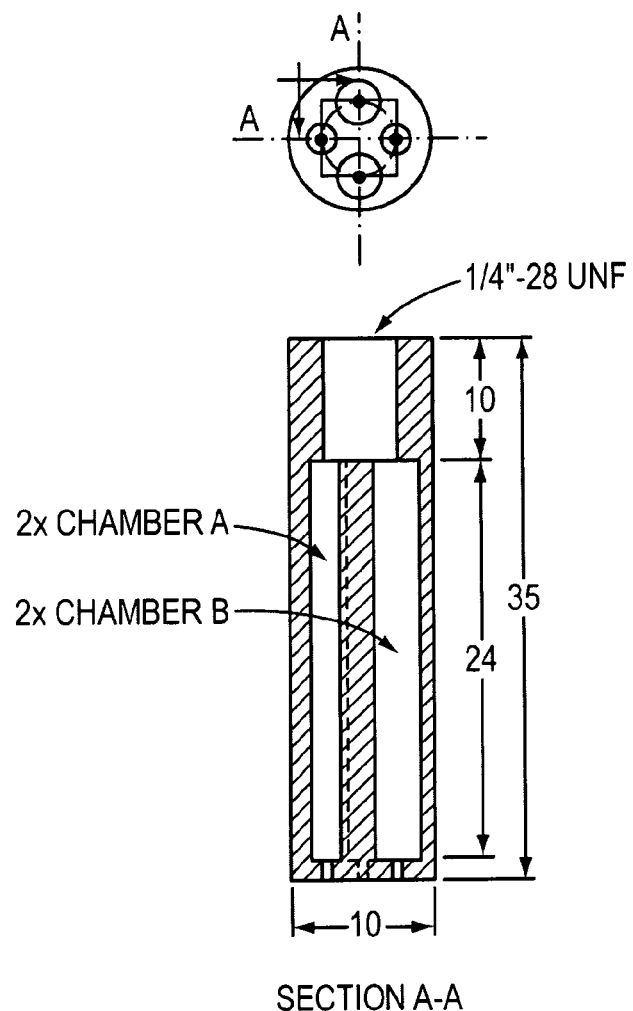
FIG. 9: Schematic representation of a plastic cartridge with four separate sample volumes, opposite (see top view) sample volumes being of equal dimensions and associated volumes (all dimensions in mm).

FIG. 9 is an example of a sample container manufactured from polymer resin using rapid prototyping methods. The container has four separate volumes in a flow-through configuration, and it includes a threaded fitting for an inlet port and a single reservoir to distribute fluid into the separate volumes.

Figure 10:
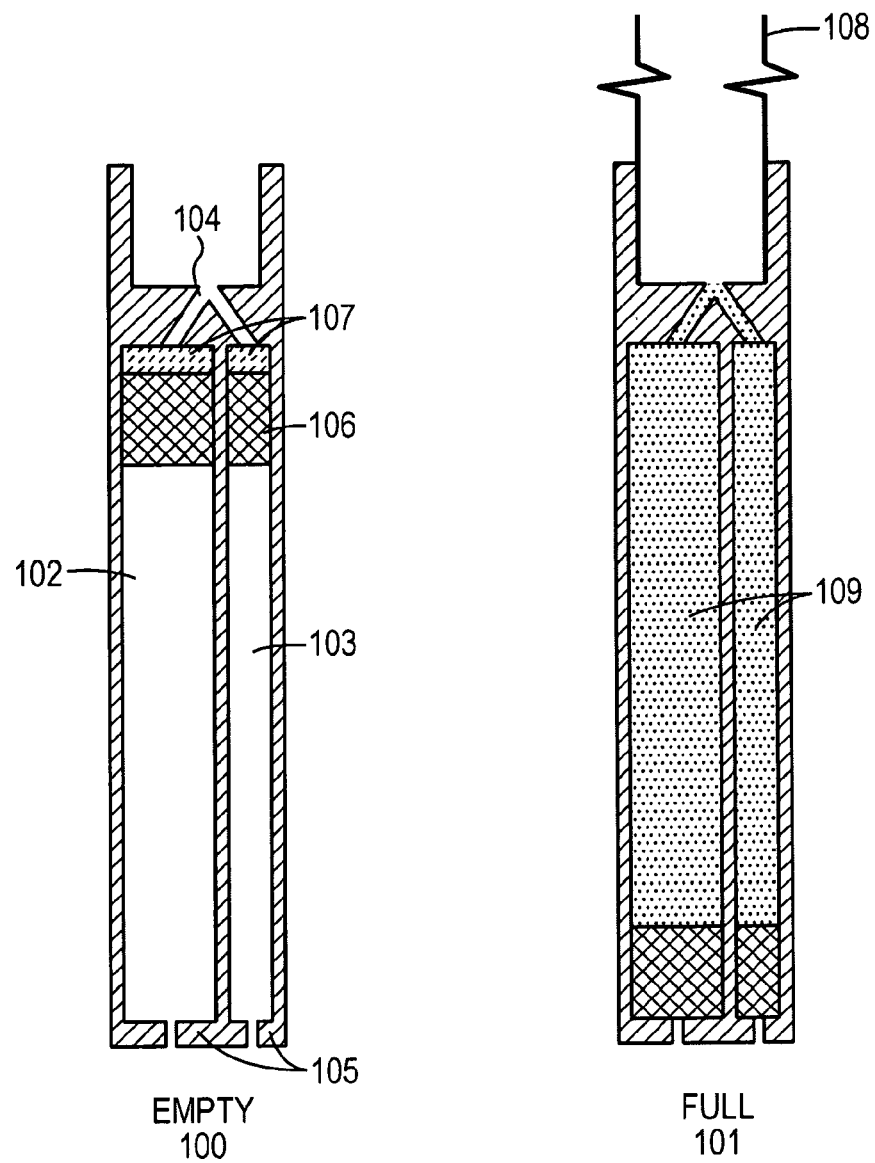
FIG. 10: Schematic representation of an empty and full plastic cartridge with two separate sample chambers.

FIG. 10 is a schematic showing both an empty (100) and a full (101) sample container. The sample container includes two separate sample chambers of different volume (102, 103), inlets or fluidic pathways (104) that are used to fill a sample into the sample container, vent holes (105), a movable barrier (black, 106) and pre-filled reagent composition (orange, 107). Using a syringe (108) a fluid to be tested is filled into the sample container, thereby moving the movable barrier (106) downwards and mixing with the reagent composition to form two separate samples containing reagent composition (light orange, 109).

Figure 11:
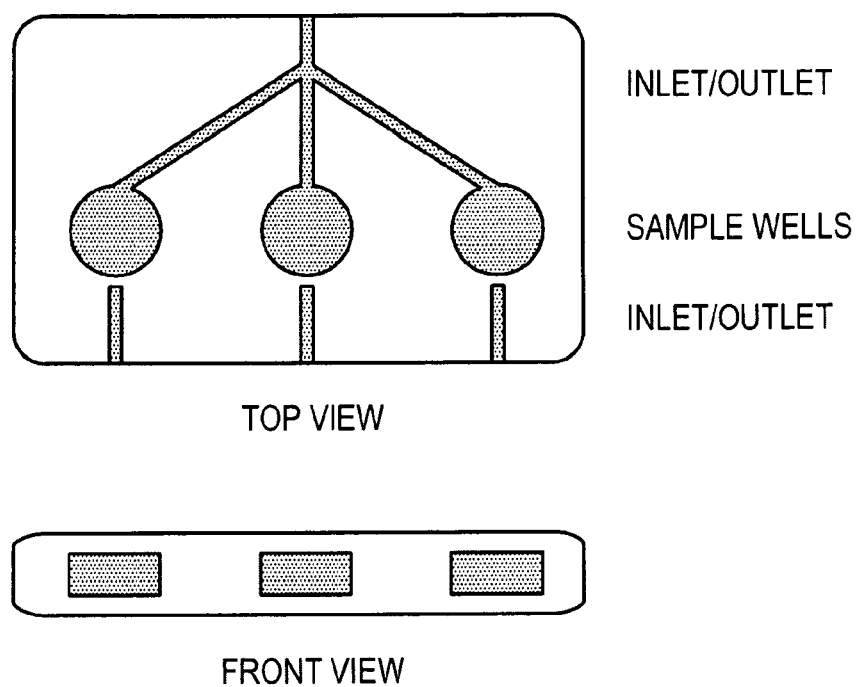
FIG. 11: Schematic of a planar cartridge.

FIG. 11 is a schematic showing a planar sample cartridge with three different wells or sample chambers that can be used, for example, with surface coils and/or Helmholtz coils.

Determination of the T2 of a sample contained in a sample container made, at least, in part of a polymeric material comprises applying a CPMG sequence to the sample and the sample container. It is believed that the CPMG sequence refocuses inhomogeneities of the magnetic field such that all of the signal within the detection coil is present in the echoes, which are acquired, in part or completely. This is unlike an FID (free induction decay) where only a fraction of the signal from the plastic may be present. The nature of the rapid decay of polymeric material in an FID yields a very low background signal in the Fourier transformed spectrum. In contrast, in relaxometry, because CPMG sequence data are typically analyzed by integrating the echoes or taking the amplitude of each echo, the CPMG signal actually contains both the plastic and liquid signal. In the context of the present invention, it has been found that one way of minimizing the contribution from the polymeric material of the sample container to the T2 of the sample is careful plastic selection, for example, to ensure that, preferably, only the first few echoes contain signal from the plastic container. The selection of suitable polymeric materials for the sample container is described below. It has further been found that the contributions due to the polymeric material of the sample container can be reduced, partly or completely, by adapting the acquisition and/or postprocessing step as described below.

In T1 signal measurement the FID signal is measured. In this case a fraction of the plastic signal (of a sample container made of a material comprising a polymeric material) is measured. In relaxometry, FID signals are typically analyzed by taking the amplitude of the first data point in the FID. Thus, in contrast to high field NMR, use of polymeric material containing sample containers in relaxometric determination of T1 is expected to lead to a signal that is a sum of the liquid signal and a fraction of a signal from the polymeric material of the sample container. In the context of the present invention, it has been found that the magnitude of this fraction is determined by the dead time of the detection electronics. One can introduce a delay to collect the FID signal after the signal from the polymeric material of the sample container has completely decayed, allowing for measurement of only the liquid signal.

Among the advantages of sample containers made of materials comprising polymeric materials and sample containers entirely made of polymeric materials is that complex sample container designs can be achieved at low cost, leading, for example, to disposable sample containers even for complex designs, for example, cartridges. Potential components that may be used in the sample container (e.g., cartridge design) include plastic, lidding, film, foil, hydrophobic vents, gasketing, and labels. Typically, any component of the sample container that will be positioned in the detection volume of an NMR device will lead to an NMR signal associated with the component. The following description provides results for a number of polymers tested for their suitability as material for the sample container or as component of the sample container.

Polymer Material Testing

All data was generated on a Bruker Minispec mq20. Sample sizes were approximately 0.2 g loaded into a 10 mm glass NMR tube, and the samples were maintained below 15 mm in height. A fid scan was acquired, and the first data point was obtained as the amplitude. A T2 CPMG pulse sequence was delivered with pulse spacing 0.25 ms, and the response was fitted to an exponential curve. A 0.2 ml reference sample of 4.5 mg/ml copper sulfate solution in a 5 mm glass tube was used to normalize intensities.

Materials were divided into categories of plastics, elastomers, adhesive films, and hydrophobic vents. Plastics were obtained as pellets or sheet form. Elastomers were cut from sheet or molded part. Adhesive films and hydrophobic vents were cut from sheet. A supplementary analysis was performed to model the impact the materials would have on measurement.

The tables in this section provide FID and T2 amplitude normalized relative to the reference sample, and T2.

A. Reference Sample

Figure 12:
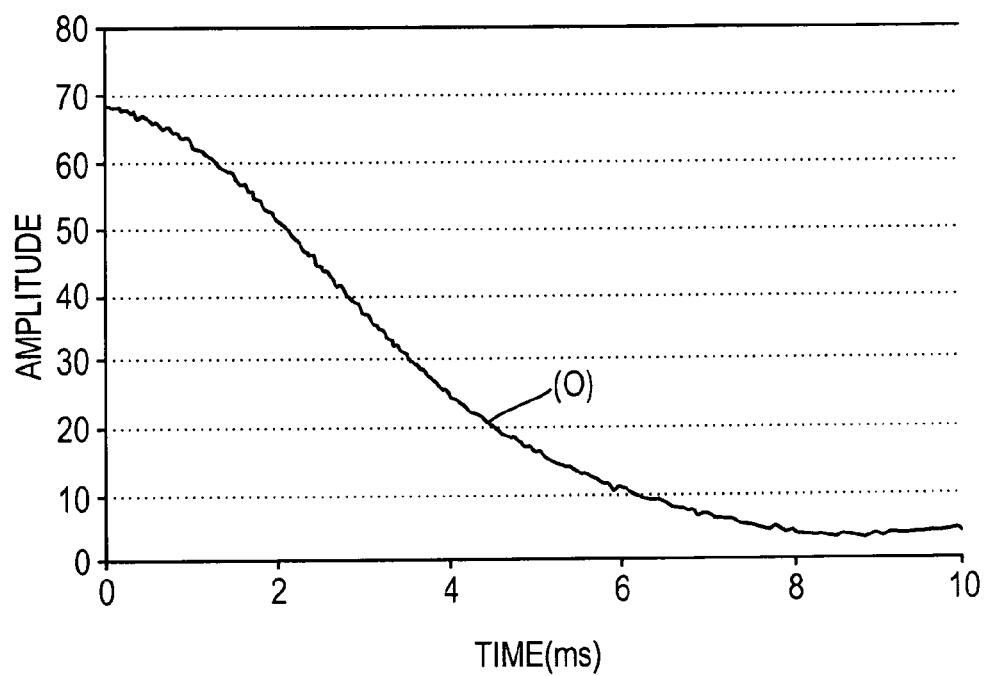
FIG. 12: Graphical representation of the free induction decay of a copper sulfate reference solution in a glass NMR tube.

The FID for the copper sulfate reference solution is shown in FIG. 12. The signal does not decay until about 10 milliseconds. The parameters for the T2 curve generated from the CPMG sequence are: Amplitude=67.1, T2=66.8 ms.

B. Plastics

Results for plastic materials are provided in below table. FID signals for the three plastics with the highest signal decayed well within 3 ms, and signal for all other plastics decayed on the order of 0.25 ms, which indicates they will have a minor contribution to signal acquired by a T2 CPMG measurement with a tau of 0.25 ms.

| Resin | Material | fid | T2 Amp | T2 (ms) |
|---|---|---|---|---|
| COC 8007S-04 | COC | 0.008 | 0.0004 | 2 |
| COP 1020R | COP | 0.016 | 0.0016 | 2 |
| COP 690R | COP | 0.012 | 0.0019 | 4 |
| COP 750R | COP | 0.010 | 0.0010 | 4 |
| HF 1110-111 | Polycarbonate | 0.023 | 0.0013 | 9 |
| PC 2458 | Polycarbonate | 0.017 | 0.0024 | 2.7 |
| PP 6823MZ | Polypropylene | 0.070 | 0.0145 | 0.6 |
| PP 7425 | Polypropylene | 0.100 | 0.0099 | 0.8 |
| PP 7825 | Polypropylene | 0.128 | 0.0246 | 0.54 |
| PS 168N | Polystyrene | 0.009 | 0.0003 | 40 |
| PS 3510 | Polystyrene | 0.007 | 0.0004 | 20 |
| PS 3900 | Polystyrene | 0.007 | 0.0003 | 30 |
| CLG960 | Acrylic PMMA | 0.020 | 0.0083 | 0.6 |
| UVT 100 | Acrylic PMMA | 0.023 | 0.0007 | 9 |
| V825IUA-100 | Acrylic PMMA | 0.026 | 0.0009 | 2 |
| VOD 100 | Acrylic PMMA | 0.025 | 0.0025 | 1.6 |
| n/a | ABS | 0.19 | 0.1593 | 1.08 |
|  | PEEK | 0.01 | 0.0009 | 6 |
|  | Polysulfone | 0.01 | 0.0071 | 0.8 |
|  | Delrin | 0.08 | 0.0086 | 2.4 |
|  | Polyester (PET) | 0.00 | 0.0013 | 5 |
|  | HDPE | n/a | 0.0074 | 0.5 |
|  | PVC | 0.01 | 0.0006 | 10 |
|  | PETG | 0.01 | 0.0019 | 3 |

C. Elastomers

Elastomers are flexible and resilient and are available in a range of hardness, measured by durometer. They can be found in a wide variety of materials; examples measured in this study are polyurethane and silicone. Additional common elastomers not included in this study are buna-N, viton, and EPDM, and they are typically found in O-rings.

| Material | Durometer | fid | T2 Amp | T2 (ms) |
|---|---|---|---|---|
| urethane | 30A | 0.544 | 0.42 | 1.46 |
|  | 40A | 0.508 | 0.42 | 0.89 |
|  | 50A | 0.452 | 0.47 | 0.46 |
|  | 60A | 0.449 | 0.47 | 0.44 |
|  | 70A | 0.451 | 0.48 | 0.45 |
|  | 80A | 0.732 | 0.76 | 0.44 |
|  | 90A | 0.560 | 0.37 | 0.4 |
|  | 95A | 0.412 | 0.25 | 0.32 |
|  | 75D | 0.166 | 0.07 | 0.34 |
| silicone | 10A | 0.651 | 0.35 | 38.90 |
|  | 20A | 0.665 | 0.34 | 35.70 |
|  | 35A | 0.538 | 0.28 | 11.30 |
|  | 55A | 0.504 | 0.35 | 10.10 |
|  | 60A | 0.621 | 0.5481 | 0.43 |
|  | 78A | 0.496 | 0.3294 | 0.38 |
|  | 88A | 0.303 | 0.1822 | 0.36 |
|  | 75D | 0.032 | 0.0020 | 2.70 |
| Versaflex ™ | 30A | 1.120 | 0.81 | 8.87 |

Materials in a range of durometer hardness were tested to determine whether the MR signal is related to hardness. The below table shows that the T2 amplitudes of elastomers are all significantly higher than observed in plastics. It is believed that this indicates a higher hydrogen density or higher hydrogen mobility. The silicones below durometer 60A were tested from a sheet and appear to have a bi-exponential pattern, which may be an indicator they are not homogeneous. Data shows a general trend of lower fid with increasing durometer, with a few outliers. The T2 amplitude does not follow the trend. Furthermore, values do not agree between different materials of same hardness. There is, however, evidence of decreasing T2 values with increasing hardness within the same material family. Therefore, factors other than hardness contribute to the NMR response.

D. Adhesive Films

All signals decayed within 3 ms, and intensities were less than 30% of the reference (see Table below).

| Film | fid | T2 Amp | T2 (ms) |
|---|---|---|---|
| PEEK 0.002" | 0.287 | 0.2045 | 0.38 |
| FEP 0.0035" | 0.166 | 0.0997 | 2 |
| PET 0.002" | 0.140 | 0.1006 | 0.45 |
| UHMWPE 0.005" | 0.270 | 0.0434 | 0.57 |

E. Hydrophobic Vents

Results are shown in the table below. PTFE signals were at noise level, which is expected because it does not contain hydrogen. HDPE (X-4904) and polypropylene (X-4911), however, were more significant; peak intensities were as high as 10% of the reference sample. All signals decayed within 0.5 ms.

| Material | Description | fid | T2 Amp | T2 (ms) |
|---|---|---|---|---|
| X-4904 | HDPE Porex | 0.104 | 0.0012 | 7 |
| X-4911 | PP Porex | 0.110 | 0.0090 | 0.5 |
| PM17Y | PTFE Mupor | 0.009 | 0.0003 | 40 |
| PM0510 | PTFE Mupor | 0.006 | 0.0002 | 0 |
| PM3010 | PTFE Mupor | 0.001 | 0.0001 | 0 |

F. Error Model

It is desirable, of course, to use materials that are "transparent" in the NMR, and have both low T2 amplitude and T2 value. However, nearly all polymers produce at least a small signal, and determining the actual threshold of acceptability ultimately depends on the amount of measurement error introduced, in particular, if steps to discriminate NMR signal associated with the sample from NMR signal associated with the NMR sample container are not desired. A mathematical model can be developed to quantify the error contribution.

The T2 decay profile for a homogeneous sample fits the exponential equation:

$$y = Ae^{-t/T2}$$

The effect of interfering material is calculated by summing a standard curve of sample A with an interfering material B, yielding the profile:

$$y = Ae^{-t/T2A} + Be^{-t/T2B}$$

For the model, sample was fixed with $A=1$ and $T2_A=100$ ms, and acquisition time was fixed at 300 ms. Monoexponential curves were fitted to the summed data with varying B and $T2_B$. A percentage error compared to T2A was calculated. Error is lowest for low amplitude and low T2, as expected. The error increases rapidly with larger T2B values even for low signal amplitudes because larger values tend to dominate the exponential fit.

All plastics tested produce an error of ≦0.5%, and only elastomers were found to exceed 1% error. For T2B/T2A below 0.025, amplitude B/A can be very high and still have low error. Also, if B/A is below 0.045, T2B/T2A can be high and still have low error.

G. Acquisition Time

Figure 13:
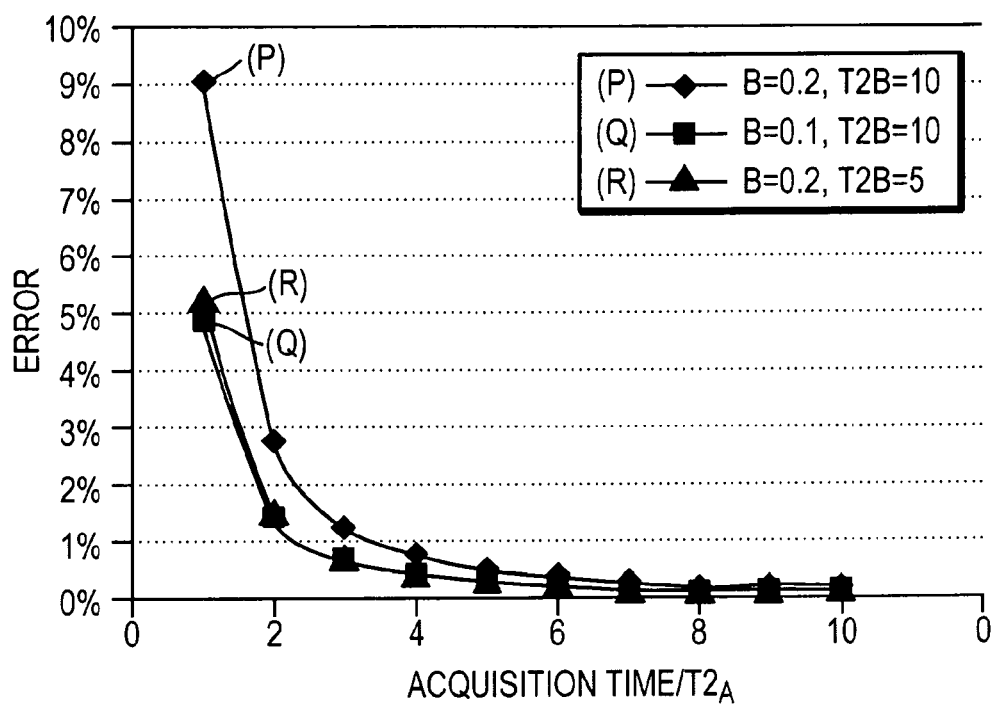
FIG. 13: Graphical representation of the error of T2 of a sample A due to containing the sample A in a sample container B made of polymeric material as a function of acquisition time for different parameter sets (B=T2 amplitude of polymeric sample container material B, $T2_B$=T2 value of polymeric sample container material B).

The error model has also been used to determine the contribution of the polymeric material NMR signal to the T2 value of the sample at varying acquisition times. FIG. 13 shows that error is highest for short acquisition times. The sample has fixed A=1, and material property parameters were varied to determine effect of different polymeric materials. Increasing the acquisition time from T2 to 3T2 reduces the error by a factor of 13. Reducing either the material amplitude or T2 value by half reduces the error by about half Changing the number of data points did not have an effect. Note that error due to noise will be additional. Thus, longer acquisition time reduce noise error and reduce error due to an interfering material.

The best-case material is completely invisible to NMR relaxation measurements. However, it has been found that most polymers, and, in particular, proton-rich polymers produce an NMR signal leading to a contribution (error) to the nuclear magnetic resonance parameter (e.g. T2) of the sample contained within a sample container made, at least in part, of the polymeric material.

It has been found in the context of this invention that the undesirable signal contribution from the polymeric material containing sample container can be reduced, partly or completely, by selection of polymeric materials with small contribution (error), by increasing acquisition time, delaying sampling, and/or processing the NMR data computationally to discriminate the NMR signal associated with the sample from the NMR signal associated with the sample container.

One embodiment of the present invention is method for obtaining a nuclear magnetic resonance parameter of a sample. The method comprises (a) applying a radiofrequency pulse sequence in the presence of a magnetic field to the sample and a sample container containing the sample, resulting in an NMR signal associated with the sample and an NMR signal associated with the sample container, wherein the sample container comprises a polymeric material; (b) acquiring part or all of the resulting NMR signals to obtain raw data; and (c) processing the resulting NMR signals to obtain the nuclear magnetic resonance parameter of the sample; and (d) reducing, partly or completely, contribution of the NMR signal associated with the sample container to the nuclear magnetic resonance parameter of the sample; wherein the nuclear magnetic resonance parameter is T1 or T2. It is to be understood, that step (d) of this method can be performed prior, during and/or after steps (a), (b) and (c). For example, the method can include the following step for reducing the contribution of the NMR signal associated with the sample container to the nuclear magnetic resonance parameter of the sample: providing a sample container comprising polymeric material(s) with low contribution prior to step (a).

The sample container and methods of the present invention allow relaxation measurements to determine nuclear magnetic resonance parameters (e.g., T1 and T2) without the need to match the bulk magnetic susceptibility (chi factor) of the polymeric material(s) of the sample container with the bulk magnetic susceptibility (chi factor) of the solvent and/or sample containing solvent (e.g., biofluid). The polymeric material(s) for the sample containers of the present invention do not need to be selected to have a bulk magnetic susceptibility (chi factor) that matches the bulk magnetic susceptibility (chi factor) of the solvent and/or sample containing solvent (e.g., biofluid). This is unlike high-field NMR in which such matching would be essential.

Further, in contrast to high-field NMR, the methods of the present invention employ low magnetic fields. Typically, maximum magnetic field strength values provided by the magnets of the nuclear magnetic devices used in the methods of the present invention are between about 0.2 Tesla and about 2 Tesla. More typically, they are between about 0.3 and about 1.5 Tesla. Even more typically, they are between about 0.4 and about 1.1 Tesla. Even more typically, they are between about 0.2 and about 1.1 Tesla. Even more typically, they are between about 0.2 and about 0.85 Tesla. Most typically, they are between about 0.45 and about 0.85 Tesla.

A further aspect of the present invention are NMR sample containers that comprise a polymeric material, wherein the sample container contains a biofluid and the sample container is adapted for measuring T1 and/or T2 in a nuclear magnetic resonance device using, for example, any one of the methods for measuring a nuclear magnetic resonance parameter described above.

A "biofluid" as used herein refers to a biological liquid of a human or animal that can be excreted (such as urine or sweat), secreted (such as breast milk or bile), obtained with a medical device, for example, a needle (such as blood, plasma, serum, tears, buffer, swab extract, cell lysate, sputum, stool, saliva, bone marrow, wash or aspirate (bronchial, nasal, tracheal), cerebrospinal fluid), or develop as a result of a pathological process (e.g., blister or cyst fluid). Typically, the biofluid is blood or plasma.

A "nuclear magnetic resonance device configured to measure T1 and/or T2" as used herein, refers to a nuclear magnetic resonance device that is set to the proper parameters to measure T1 and/or T2.

The sample container of the present invention can be made in part or entirely out of polymeric material. Typically, the sample container comprises at least 10% by weight of polymeric material. More typically, the sample container comprises at least 50% by weight of polymeric material. Even more typically, the sample container comprises at least 80% by weight of polymeric material. Even more typically, the sample container comprises at least 90% by weight of polymeric material.

A "predetermined estimate of the T2 of a sample" as used herein, refers to an experimental or theoretical estimate of the T2 value of the sample. Experimentally, the predetermined estimate of the T2 of the sample can be obtained with nuclear magnetic resonance devices as known in the art while the sample is contained in a glass NMR tube and a CPMG sequence is applied to the sample.

A "predetermined estimate of the T2 amplitude of a sample" as used herein, refers to an experimental or theoretical estimate of the T2 amplitude of the sample. Experimentally, the predetermined estimate of the T2 amplitude of the sample can be obtained with nuclear magnetic resonance devices as known in the art while the sample is contained in a glass NMR tube and a CPMG sequence is applied to the sample.

Polymeric materials suitable as sample container material include but are not limited to cyclic olefin copolymers, cyclo olefin polymers, polycarbonates, polypropylene, polystyrene, poly(methyl methacrylate), polyetheretherketone, polyketone, polysulfone, polyoxymethylene, polyethylene terephthalate, polyethylene, polyvinyl chloride, polyurethanes and acrylonitrile butadiene styrene.

More typically, the polymeric material is a plastic, for example, a cyclic olefin copolymer, a cyclo olefin polymer, a polycarbonate, polypropylene, polystyrene, poly(methyl methacrylate), polyetheretherketone, polyketone, polysulfone, polyoxymethylene, polyethylene terephthalate, polyethylene, or polyvinyl chloride A preferred polymeric material is polyoxymethylene.

"Magnetic particles" as used herein, are particles that respond to or are influenced by a sample characteristic to correlate the presence and/or extent of the sample characteristic with the presence, change or magnitude of the magnetic resonance signals associated with the sample. Typically, the magnetic particles respond by aggregating. Also, typically, magnetic particles have an average particle size of between about 1 nm and 10 µm, more typically, between about 1 nm and about 5 µm, most typically, between about 5 nm and 1 µm. Magnetic particles are magnetic, more typically, paramagnetic or superparamagnetic, preferably, superparamagnetic. They can have binding moieties on their surface. The binding moieties are preferably operative to alter the aggregation of the magnetic particles as a function of the presence or concentration of the analyte. The magnetic particles may include an oxide and/or a hydroxide of Fe, Si, Sn, An, Ti, Bi, Zr, and/or Zn. The magnetic particles are preferably superparamagnetic and have crystallite size from about 1 nm to about 100 nm. The magnetic nanoparticles preferably have a metal oxide core of about 1 to about 25 nm, from about 3 to about 10 nm, or about 5 nm in diameter. The binding moieties may include one or more species of one or more of the following: an amino acid, a nucleic acid, an oligonucleotide, a therapeutic agent, a metabolite of a therapeutic agent, a peptide, a polypeptide, a protein, a carbohydrate, a polysaccharide, a virus, and/or bacteria. For example, in one embodiment, the binding moieties may include one, two, or more types of oligonucleotides and/or one, two, or more types of proteins. The binding moieties may be a polymer, or may be part of a polymer that is linked to, or otherwise associated with one or more of the magnetic particles. The binding moieties preferably include functional groups, for example, the binding moieties may include one or more species of one or more of the following: an amino group, a carboxyl group, a sulfhydryl group, an amine group, an imine group, an epoxy group, a hydroxyl group, a thiol group, an acrylate group, and/or an isocyano group.

The analyte may include or be one or more species of one or more of the following: a protein, a peptide, a polypeptide, an amino acid, a nucleic acid, an oligonucleotide, a therapeutic agent, a metabolite of a therapeutic agent, RNA, DNA, an antibody, an organism, a virus, bacteria, a carbohydrate, a polysaccharide, and glucose. The analyte may also include or be, for example, a lipid, a gas (e.g., oxygen, carbon dioxide), an electrolyte or ion (e.g., sodium, potassium, chloride, bicarbonate, BUN, creatinine, glucose, magnesium, phosphate, calcium, ammonia, lactate), a lipoprotein, cholesterol, a fatty acid, a glycoprotein, a proteoglycan, a lipopolysaccharide, and/or a small molecule.

Magnetic particles may form one or more discrete populations of clusters, each of the populations being characterized by a cluster size. The number of different cluster populations (also herein number of clusters) and the corresponding cluster sizes depend on a number of factors including binding affinities between binding moieties and analytes, valency of binding moieties and analytes and the number of binding moieties per magnetic particle, and can be changed using methods known in the art.

Magnetic particles comprising binding moieties that bind to analytes, respond to the presence of analyte by binding with the analytes through the binding moieties, thereby forming clusters of magnetic particles (i.e., agglomerating). In contrast, dispersion based MRSw assays are based on MRSw assay compositions containing pre-formed clusters of magnetic particles in which the magnetic particles are not bound to each other through analyte but through other binding agents. Presence of analyte leads in these dispersion based MRSw assay compositions to dispersion of the pre-formed clusters; as with agglomeration MRSw assays this dispersion may follow a monodisperse or polydisperse model. A further MRSw assay format is referred to as competitive agglomerative where the analyte inhibits the aggregation of the magnetic particles by competing for binding to an agent present in the assay formulation. In this case in the absence of analyte magnetic particles cluster and with high amounts of analytes dispersed magnetic particles are obtained.

The methods described herein can form or be part of MRSw assays, for example, as described above. Also, the sample containers of the present invention are suitable for MRSw assays, for example, as described herein.

While this invention has been particularly shown and described with references to example embodiments thereof, it will be understood by those skilled in the art that various changes in form and details may be made therein without departing from the scope of the invention encompassed by the appended claims.

What is claimed is:

1. A method for obtaining a T2 time domain signal of a blood sample, the method comprising using a nuclear magnetic resonance device to perform the steps of:
(a) applying a radiofrequency CPMG pulse sequence in the presence of a magnetic field of from 0.2 to 2.0 Tesla to the blood sample having an estimated T2 value and a sample container containing the blood sample, resulting in an NMR signal associated with the blood sample and an NMR signal associated with the sample container, wherein the sample container comprises a polymeric material, and wherein the contribution of the NMR signal associated with the sample container to the T2 time domain signal of the blood sample is reduced by using a CPMG pulse sequence having acquisition time greater than five times the estimated T2 value of the blood sample;
(b) acquiring the resulting NMR signals to obtain raw data; and
(c) processing the resulting NMR signals to obtain the T2 time domain signal of the blood sample,
wherein the estimated T2 value of the blood sample is determined, prior to step (a), by (i) using a nuclear magnetic resonance device to acquire NMR signals of the blood and a sample container containing the blood sample to produce whole raw data, (ii) using a processor to computationally discriminate a contribution from the sample container to the whole raw data to obtain sample data, partly or completely, free of the contribution from the sample container; and (iii) calculating from the sample data the estimated T2 value of the blood sample.

2. The method of claim 1, wherein the material of the sample container comprises more than 90% by weight of the sample container of the one or more polymeric materials.

3. The method of claim 1, wherein the sample container further contains magnetic particles functionalized with binding moieties, the binding moieties being able to bind to analyte in the blood sample, the method further comprising the step of exposing the blood sample container to conditions suitable for the binding moieties and analyte in the blood sample to bind prior to acquisition of the NMR signals.

4. The method of claim 3, wherein the analyte comprises at least one member selected from the group consisting of a protein, a peptide, a polypeptide, an amino acid, a nucleic acid, an oligonucleotide, a therapeutic agent, a metabolite of a therapeutic agent, RNA, DNA, an antibody, an organism, a virus, a bacteria, a carbohydrate, a polysaccharide, glucose, an ion or a small molecule.

5. The method of claim 3, wherein the binding moieties are oligonucleotide binding moieties, polypeptide binding moieties, antibody binding moieties or polysaccharide binding moieties or synthetic small molecule binding moieties.

* * * * *